(12) United States Patent
Ukawa et al.

(10) Patent No.: US 10,010,292 B2
(45) Date of Patent: Jul. 3, 2018

(54) MEASURING APPARATUS AND MEASURING METHOD

(71) Applicant: NIHON KOHDEN CORPORATION, Tokyo (JP)

(72) Inventors: Teiji Ukawa, Tokyo (JP); Haruka Morimoto, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 218 days.

(21) Appl. No.: 14/996,924

(22) Filed: Jan. 15, 2016

(65) Prior Publication Data
US 2016/0213332 A1 Jul. 28, 2016

(30) Foreign Application Priority Data
Jan. 28, 2015 (JP) .................. 2015-013807

(51) Int. Cl.
- A61B 5/022 (2006.01)
- A61B 5/0295 (2006.01)
- A61B 5/0205 (2006.01)
- A61B 5/00 (2006.01)
- A61B 5/021 (2006.01)
- A61B 5/024 (2006.01)

(52) U.S. Cl.
CPC ............ *A61B 5/7278* (2013.01); *A61B 5/022* (2013.01); *A61B 5/0205* (2013.01); *A61B 5/0295* (2013.01); *A61B 5/02116* (2013.01); *A61B 5/02233* (2013.01); *A61B 5/02422* (2013.01)

(58) Field of Classification Search
CPC . A61B 5/7278; A61B 5/0205; A61B 5/02116; A61B 5/022; A61B 5/02233; A61B 5/0295; A61B 5/02422

USPC .............. 600/481, 483, 484, 485, 486, 488, 600/490–504
See application file for complete search history.

(56) References Cited

U.S. PATENT DOCUMENTS

| | | | | | |
|---|---|---|---|---|---|
| 5,810,734 | A | * | 9/1998 | Caro .................... | A61B 5/022 600/301 |
| 5,830,131 | A | * | 11/1998 | Caro .................. | A61B 5/02108 600/300 |
| 5,833,618 | A | * | 11/1998 | Caro .................. | A61B 5/02108 600/300 |
| 6,045,509 | A | * | 4/2000 | Caro .................. | A61B 5/02133 600/481 |

(Continued)

FOREIGN PATENT DOCUMENTS

| | | |
|---|---|---|
| JP | 2002-524177 A | 8/2002 |
| JP | 2012-040088 A | 3/2012 |

OTHER PUBLICATIONS

European Search Report for Application No. EP 16 15 1343 dated Jun. 21, 2016.

*Primary Examiner* — Navin Natnithithadha
(74) *Attorney, Agent, or Firm* — Pearne & Gordon LLP (57) ABSTRACT

An apparatus and a method for measuring a respiration-induced blood pressure fluctuation are provided. A blood pressure calculating section calculates a pulse pressure of a subject. A pulse wave measuring section measures a pulse wave of the subject. A respiration-induced fluctuation calculating section calculates the respiration-induced blood pressure fluctuation of the subject as a pressure value, based on the pulse pressure and a fluctuation and an amplitude of the pulse wave in a given time period.

11 Claims, 8 Drawing Sheets

(56) References Cited

U.S. PATENT DOCUMENTS

| | | | |
|---|---|---|---|
| 6,129,675 A | 10/2000 | Jay | |
| 6,325,761 B1 | 12/2001 | Jay | |
| 6,371,921 B1* | 4/2002 | Caro | A61B 5/02133 600/485 |
| 6,852,083 B2* | 2/2005 | Caro | A61B 5/022 600/485 |
| 7,163,512 B1* | 1/2007 | Childre | A61B 5/024 600/26 |
| 7,462,151 B2* | 12/2008 | Childre | A61B 5/024 600/300 |
| 8,647,282 B2* | 2/2014 | Shih | A61B 5/02225 600/481 |
| 2002/0095090 A1* | 7/2002 | Caro | A61B 5/02133 600/485 |
| 2005/0192500 A1* | 9/2005 | Caro | A61B 5/02133 600/485 |
| 2006/0189872 A1 | 8/2006 | Arnold | |
| 2011/0054331 A1* | 3/2011 | Shih | A61B 5/02225 600/494 |
| 2011/0060531 A1 | 3/2011 | Sugo et al. | |
| 2012/0046561 A1 | 2/2012 | Usuda et al. | |

* cited by examiner

MEASURING APPARATUS AND MEASURING METHOD

CROSS-REFERENCE TO RELATED APPLICATION(S)

The present application claims priority from Japanese Patent Application No. 2015-013807 filed on Jan. 28, 2015, the entire content of which is incorporated herein by reference.

BACKGROUND

The presently disclosed subject matter relates to a measuring apparatus and a measuring method, in particular, a measuring apparatus and a measuring method related to respiration-induced fluctuations in blood pressure.

Pulsus paradoxus (hereinafter, "PP") is a respiration-induced fluctuation in systolic blood pressure exceeding 10 mmHg. PP is used in determining asthma, chronic obstructive pulmonary disease (COPD), cardiac tamponade, and the like (see, e.g., Bandinelli G, et al., "Pulsus Paradoxus: an inderused tool," Intern Emerg Med (2007) 2: p. 33-35). In the National Asthma Education and Prevention Program (NAEPP), a guideline for acute asthma, for example, PP exceeding 12 mmHg is defined as a level at which treatment in a hospital is required (see, e.g., James Rayner, et al., "Continuous Noninvasive Measurement of Pulsus Paradoxus Complements Medical Decision Making in Assessment of Acute Asthma Severity," Chest. 2006 September; 130(3): p. 754-765).

As described above, the detection of PP is considered to be important in determining asthma and the like. Therefore, accurate detection of a measurement value of a respiration-induced blood pressure fluctuation is very important. Hereinafter, some related art methods for measuring respiration-induced blood pressure fluctuations will be described.

A first example is a measuring method using a Korotkoff sound. In this method, when the blood pressure is to be measured by the auscultatory method, the respiration-induced blood pressure fluctuation is calculated by measuring the difference, between the expiratory and inspiratory phases, of the cuff pressure at which a Korotkoff sound begins to be heard. This method, however, has problems in that it requires a skill of a doctor making a diagnosis and that accuracy is low (see, e.g., James Rayner, et al. and also Gregory D. Jay, et al., "Analysis of Physician Ability in the Measurement of Pulsus Paradoxus by Sphygmomanometry," Chest. 2000; 118(2): p. 348-352).

James Rayner, et al. also discloses a method for measuring a respiration-induced blood pressure fluctuation by using a non-invasive continuous blood pressure monitor. In this method, a tonometry method and a volume compensation method that are practically used in a continuous blood pressure monitor are used. However, the tonometry method and the volume compensation method require an apparatus having a complicated sensor structure and a complex pressure control, and such an apparatus is very expensive. Therefore, the tonometry method and the volume compensation method are not being widely used.

Dale W. Steele, et al. discloses a method for measuring a respiration-induced fluctuation by using the peripheral volume pulse wave acquired by a pulse oximeter (Dale W. Steele, et al., "Continuous Noninvasive Determination of Pulsus Paradoxus: A Pilot Study," ACADEMIC EMERGENCY MEDICINE, October 1995, VOL. 2/No. 10, p. 894-900). In this method, however, a ratio of the respiration-induced blood pressure fluctuation to the pulse wave amplitude is obtained, but a pressure equivalent measurement value is not obtained. Because the respiration-induced blood pressure fluctuation is not calculated as a pressure equivalent measurement value, this method is difficult to be used in determining diagnostic strategies by doctors. Moreover, the respiration-induced fluctuation calculated by this method has less correlation with the respiration-induced fluctuation calculated by an invasive method, as compared with the respiration-induced fluctuation calculated by a commercially available continuous blood pressure monitor using the volume compensation method.

JP2002-524177A discloses an apparatus for calculating a respiration-induced fluctuation of the volume pulse wave as a pressure equivalent measurement value. In this apparatus, pulse-wave waveforms in which the measurement values of PP are given are predefined (see, e.g., paragraph 0039 of JP2002-524177A). Then, the apparatus compares the predefined pulse-wave waveforms with a pulse-wave waveform measured from the subject, thereby calculating a measurement value of PP.

That is, the apparatus of JP2002-524177A is configured such that pulse-wave waveforms correlated with the respective measurement values of PP are predefined and then stored. However, it is difficult to predefine the pulse-wave waveforms and their associated measurement values of PP. In other words, a prior calibration is required, but it is difficult to perform such a calibration.

SUMMARY

Illustrative aspects of the present invention provide a measuring apparatus and a measuring method, capable of calculating a pressure equivalent of a respiration-induced blood pressure fluctuation without a prior calibration or costly configuration.

According to an illustrative aspect of the present invention, a measuring apparatus includes a blood pressure calculating section configured to calculate a pulse pressure of a subject, a pulse wave measuring section configured to measure a pulse wave of the subject, and a respiration-induced fluctuation calculating section configured to calculate a respiration-induced blood pressure fluctuation of the subject as a pressure value, based on the pulse pressure and a fluctuation and an amplitude of the pulse wave in a given time period.

According to another illustrative aspect of the present invention, a measuring method includes calculating a pulse pressure of a subject, measuring a pulse wave of the subject, and calculating a respiration-induced blood pressure fluctuation of the subject as a pressure value, based on the pulse pressure and an amplitude of the pulse wave in a given time period.

According to another illustrative aspect of the present invention, a program causes a computer to execute a method including calculating a pulse pressure of a subject, measuring a pulse wave of the subject, and calculating a respiration-induced blood pressure fluctuation of the subject as a pressure value, based on the pulse pressure and an amplitude of the pulse wave in a given time period. The program may be stored in a non-transitory computer readable medium.

DETAILED DESCRIPTION

Figure 1:
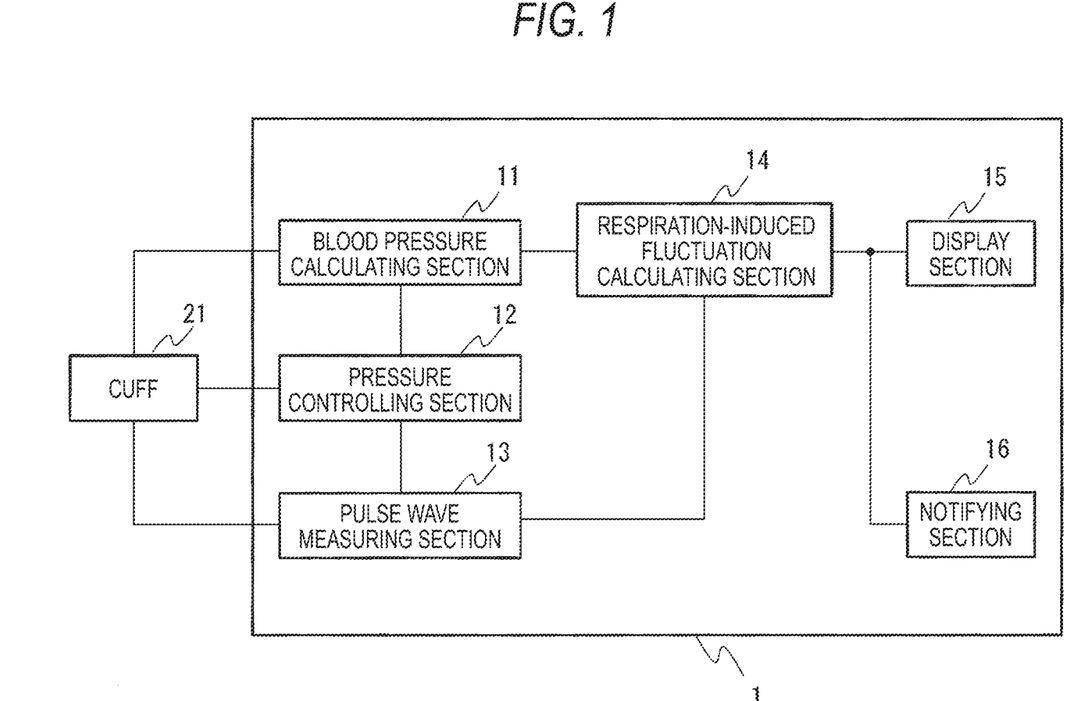
FIG. 1 is a block diagram of a configuration of a measuring apparatus according to an exemplary embodiment of the present invention.

Hereinafter, an exemplary embodiment of the invention will be described with reference to the drawings. FIG. 1 is a block diagram showing the configuration of a measuring apparatus of the exemplary embodiment. The measuring apparatus 1 includes a blood pressure calculating section 11, a pressure controlling section 12, a pulse wave measuring section 13, a respiration-induced fluctuation calculating section 14, a display section 15, and a notifying section 16. For example, the measuring apparatus 1 may be a patient monitor, a medical telemeter, an electrocardiogram, or the like.

The cuff 21 is attached to a predetermined portion (preferably, the upper arm) of the subject. The pressure controlling section 12 performs a control of raising and lowering the pressure in a similar manner as a general blood pressure measurement using the cuff 21 (such as blood pressure measurement by the oscillometric method). The blood pressure calculating section 11 calculates the systolic blood pressure and the diastolic blood pressure by using the general oscillation method or the like. The blood pressure calculating section 11 subtracts the diastolic blood pressure from the systolic blood pressure to calculate the pulse pressure. The blood pressure calculating section 11 supplies the measurement value of the calculated pulse pressure to the respiration-induced fluctuation calculating section 14.

The pulse wave measuring section 13 is configured to non-invasively measure a pulse wave of the subject. During the measurement of the pulse wave, the pressure controlling section 12 maintains the cuff 21 at a constant pressurizing force. The pressure applied to the cuff 21 has a fixed pressure value (e.g., 40 to 50 mmHg) which is equal to or lower than the diastolic blood pressure of the subject, and which is within a range that does not contain the pulse wave component of the vein. The pressure equal to or lower than the diastolic blood pressure of the subject is equal to or lower than 50 mmHg. The pulse wave measuring section 13 detects the cuff pressure under this environment. The pulse wave of the subject is superimposed on the cuff pressure. The pulse wave measuring section 13 performs a signal process on the detected cuff pressure to acquire the pulse wave superimposed on the cuff pressure (hereinafter, such a pulse wave will be referred to as the cuff pressure pulse wave). The pulse wave measuring section 13 sends the acquired cuff pressure pulse wave to the respiration-induced fluctuation calculating section 14.

The respiration-induced fluctuation calculating section 14 is configured to calculate the respiration-induced blood pressure fluctuation as a pressure value from the pulse pressure and a fluctuation and an amplitude of the cuff pressure pulse wave. The principle of calculating the respiration-induced blood pressure fluctuation as a pressure value will be described. Firstly, the principle of the blood pressure measurement by the general oscillometric method will be described with reference to FIGS. 2 and 3.

Figure 2:
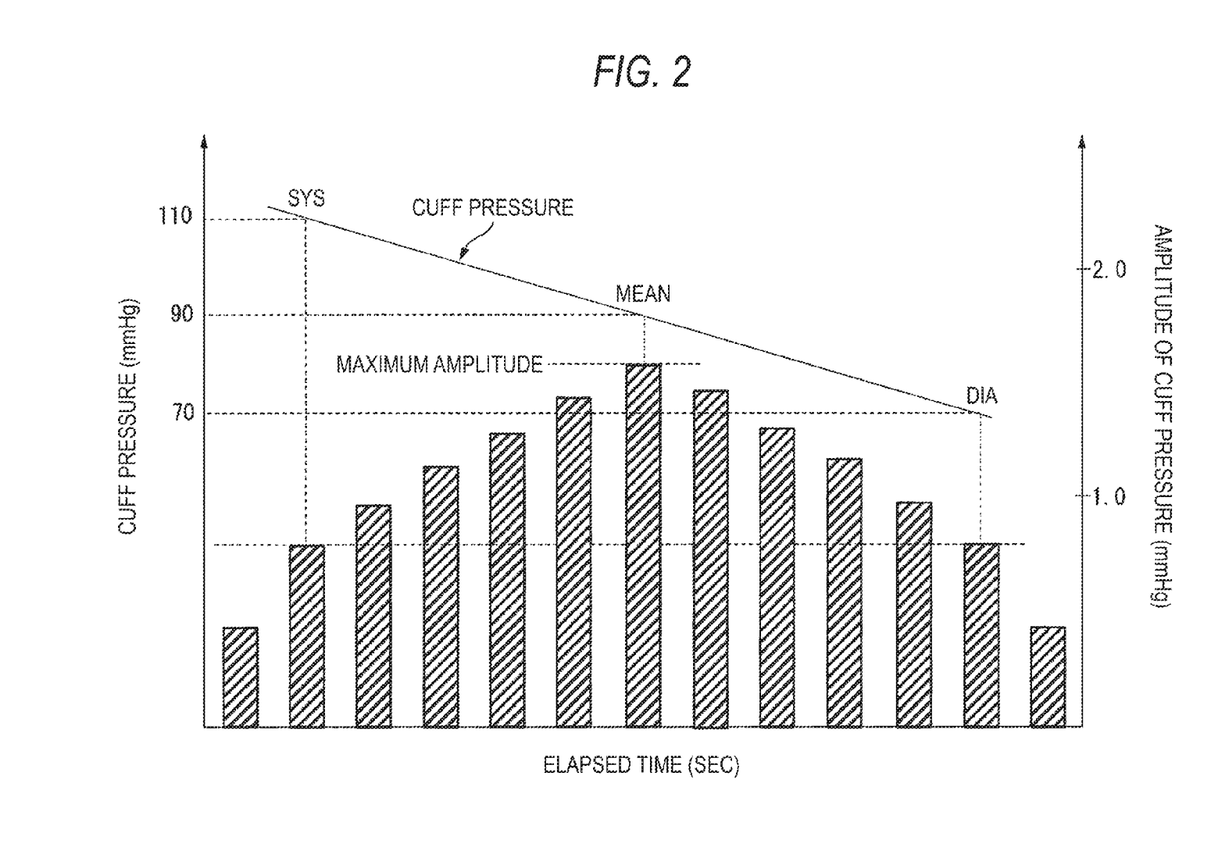
FIG. 2 is a diagram illustrating relationships between a change of a cuff pressure and a fluctuation of a cuff pressure pulse wave.

FIG. 2 is a diagram illustrating relationships between a change of the cuff pressure and a fluctuation of the cuff pressure pulse wave. The pressure controlling section 12 changes the pressurizing force applied by inflating the cuff 21, within the pressure range from a pressure which is higher than the systolic blood pressure, to that which is lower than the diastolic blood pressure. At the timing when the pressurizing force reaches the systolic blood pressure, the amplitude of the cuff pressure pulse wave which is superimposed on the cuff pressure is increased, thereafter further increased, and then again reduced. In the vicinity of the diastolic blood pressure, then, the amplitude of the cuff pressure pulse wave is rapidly reduced. The blood pressure calculating section 11 detects the fluctuation pattern of the cuff pressure pulse wave, and calculates the systolic blood pressure and the diastolic blood pressure. The fluctuation of the amplitude of the cuff pressure pulse wave reflects the degree of the volumetric change of an arterial vessel.

Figure 3:
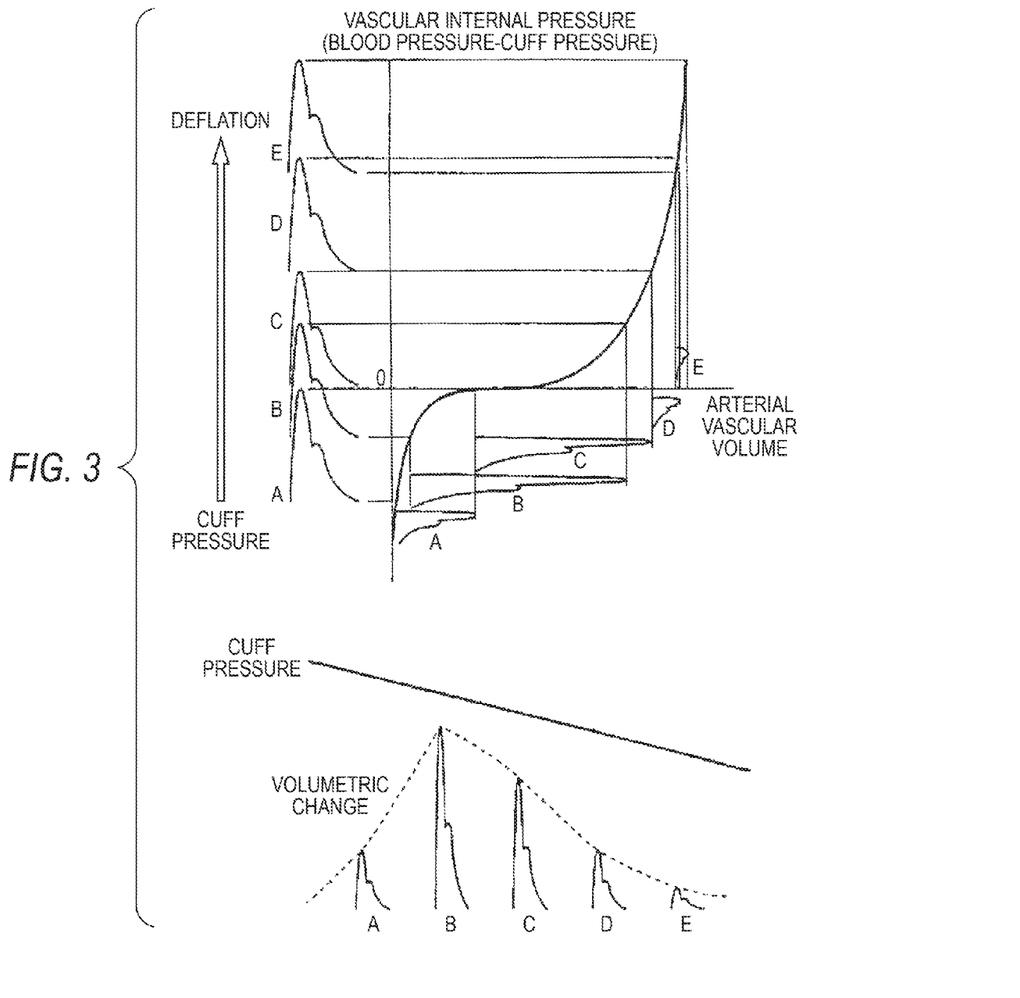
FIG. 3 is a diagram illustrating relationships between a pressure and a volume of an arterial vessel.

FIG. 3 is a diagram illustrating relationships between the pressure and volume of an arterial vessel (extract from Hideaki Shimizu, "Kenko o Sasaeru Iryokiki Kaman de Oku no Fukai Ketsuatsu Sokutei (Medical instruments supporting health. Simple sphygmomanometry having profound meaning.)" Clin. Eng. Vol. 9 No. 1, p. 26-33). The ordinate of the figure indicates the vascular internal pressure, and the abscissa indicates the volume of an arterial vessel (hereinafter, arterial vascular volume). In the case where the pressure applied to the cuff 21 is higher than the diastolic blood pressure, a blood vessel in which the internal pressure is equal to or lower than the applied pressure is closed. Therefore, a change of the arterial vascular volume shows a discontinuous waveform. Therefore, the relationship between (the value which is obtained by subtracting the cuff pressure from the blood pressure) and (the arterial vascular volume) is a nonlinear relationship as shown in FIG. 3.

In the case where the applied pressure of the cuff 21 is lower than the diastolic blood pressure, however, a change of the arterial vascular volume shows a shape which is similar to the blood pressure waveform. In the range where the applied pressure of the cuff 21 is lower than the diastolic blood pressure (D or E of FIG. 3), therefore, a change of the arterial vascular volume and a blood pressure change have an approximately linear relationship.

A fluctuation of the cuff pressure pulse wave is caused by a change of the cuff volume due to a change of the arterial vascular volume. When the cuff pressure is indicated by P, the cuff volume is indicated by V, a change of the cuff volume due to a change of the arterial vascular volume is indicated by $\Delta V$, and the amplitude of the cuff pressure pulse wave is indicated by $\Delta P$, the following expression (1) holds in accordance with Boyle-Charles's Law.

$$P \times V = (P + \Delta P) \times (V - \Delta V) \qquad (1)$$
$$= P \times V + \Delta P \times V - P \times \Delta V - \Delta P \times \Delta V$$

The values of $\Delta P$ and $\Delta V$ are smaller than those of P and V. Even when the term of $\Delta P \times \Delta V$ in the expression (1)

above is neglected, therefore, little influence is exerted. Consequently, the following expressions (2) and (3) are generally satisfied.

$$\Delta P \times V = \Delta V \times P \quad (2)$$

$$\Delta P = \Delta V \times P / V \quad (3)$$

When it is assumed that P and V are constant in the expressions (2) and (3), $\Delta P$ is proportional to $\Delta V$. That is, it is possible to consider that the amplitude $\Delta P$ of the cuff pressure pulse wave has a similarity relationship to a change of the arterial vascular volume.

The following is a summary of the above description.

Characteristic 1—a change of the arterial vascular volume is in approximately linear relationship with that of the blood pressure (in a range where the cuff pressure is equal to or lower than the diastolic blood pressure.

Characteristic 2—the amplitude of the cuff pressure pulse wave has a similarity relationship to a change of the arterial vascular volume.

In view of the above two characteristics, there is a correlation between the amplitude of the cuff pressure pulse wave and a change in the blood pressure. Therefore, the respiration-induced fluctuation calculating section 14 calculates the respiration-induced blood pressure fluctuation as a pressure value by using the cuff pressure pulse wave and the pulse pressure (blood pressure value). This will be described in detail with reference to FIGS. 4 and 5.

Figure 4:
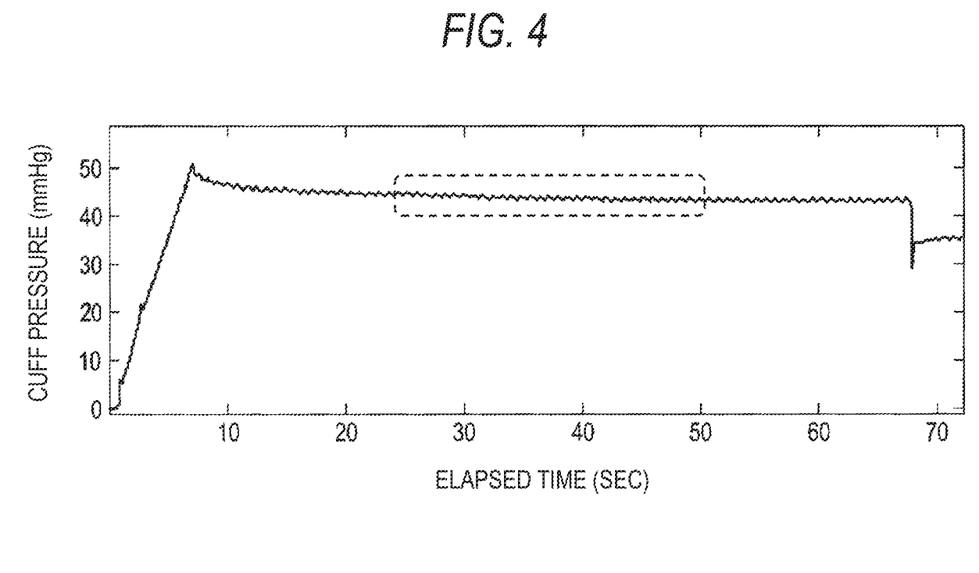
FIG. 4 is a diagram illustrating a cuff pressure in a case where an applied pressure is maintained at about 45 mmHg.

FIG. 4 is a diagram illustrating the cuff pressure in the case where the applied pressure is maintained at about 45 mmHg. The pulse wave measuring section 13 acquires the cuff pressure for about one minute, and then supplies the cuff pressure to the respiration-induced fluctuation calculating section 14. As shown in the broken-line portion of FIG. 4, the cuff pressure is varied.

Figure 5:
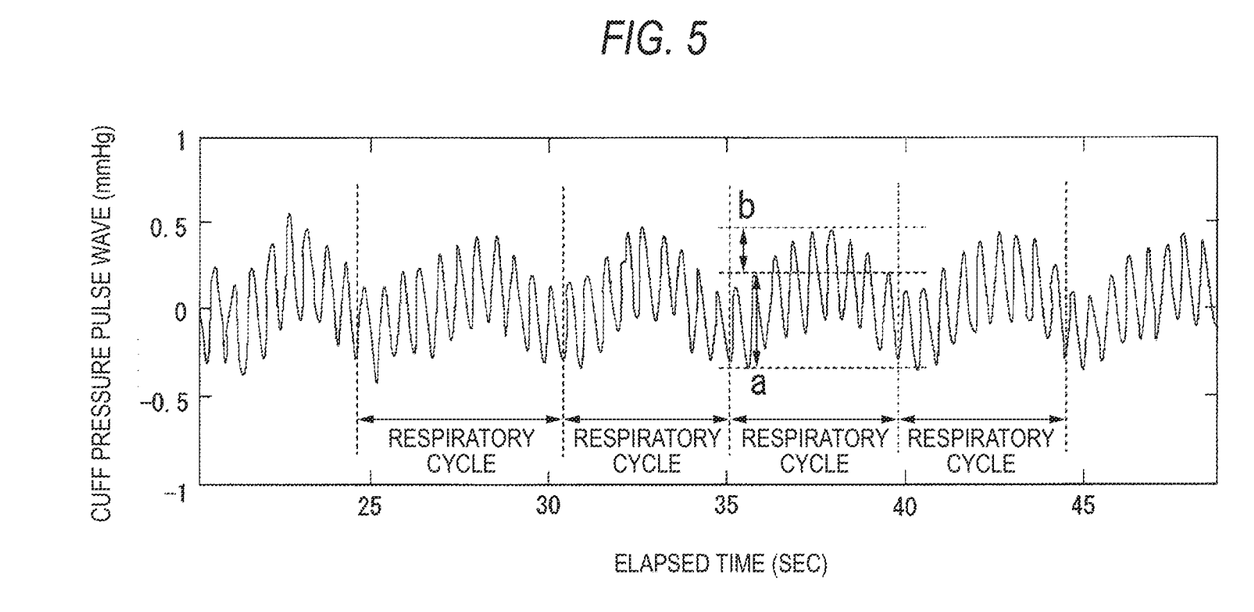
FIG. 5 is a diagram illustrating a cuff pressure pulse wave acquired by filtering the cuff pressure in a broken-line portion of FIG. 4.

FIG. 5 shows a cuff pressure pulse wave (corresponding to the broken-line portion of FIG. 4) which is acquired by filtering the cuff pressure shown in FIG. 4. The pressure which is highest during one heart beat is the maximum blood pressure (systolic blood pressure), and the lowest pressure is the minimum blood pressure (diastolic blood pressure). The pulse pressure is the difference between the systolic blood pressure and the diastolic blood pressure. That is, in FIG. 5, the amplitude a corresponds to the pressure difference in one heart beat, i.e., the pulse pressure, and the amplitude b corresponds to a respiration-induced fluctuation in pressure value. The respiration-induced fluctuation calculating section 14 calculates the respiration-induced blood pressure fluctuation as a pressure value from the pulse pressure value and the magnitudes of the fluctuation and the amplitude of the pulse wave. In a detailed calculation example, the respiration-induced fluctuation calculating section 14 calculates the respiration-induced blood pressure fluctuation (RF) as a pressure value by the following expression (4) using the pulse pressure and a ratio X (the ratio of the respiration-induced blood pressure fluctuation to the pulse pressure). In the following expression (4), Psys is the the systolic blood pressure of the subject, and Pdia is the diastolic blood pressure of the subject.

$$RF \text{ (mmHg)} = (P\text{sys} - P\text{dia}) \times \text{Ratio } X \quad (4)$$

Ratio $X = b/a$

Preferably, the respiration-induced fluctuation calculating section 14 detects the respiratory cycle such as shown in FIG. 4, and calculates the respiration-induced blood pressure fluctuation as a pressure value using the amplitude in one respiratory cycle. In other words, the respiration-induced fluctuation calculating section 14 preferably detects the amplitudes a and b in one respiratory cycle. Therefore, the respiration-induced fluctuation calculating section 14 can accurately acquire the blood pressure fluctuation induced by one respiration as a pressure value.

In the case where an artificial respirator is connected to the subject, for example, the respiratory cycle of the subject may be acquired from the control value of the artificial respirator. Alternatively, a configuration where a doctor or the like inputs the respiratory cycle of the subject from the outside may be employed. In the case where the measuring apparatus 1 has a function which can measure the respiratory cycle, the respiratory cycle may be identified by the respiratory rate that is acquired by the function. Alternatively, the respiration-induced fluctuation calculating section 14 may detect the fluctuation pattern of the cuff pressure pulse wave, and identify the respiratory cycle according to the detected fluctuation pattern.

The detection of the respiratory cycle causes the throughput to increase. Therefore, the respiration-induced blood pressure fluctuation can be calculated as a pressure value without calculating the respiratory cycle. For example, the respiration-induced fluctuation calculating section 14 may assign the amplitude at which the cuff pressure pulse wave is minimum between elapsed times of 25 to 45 seconds, and the maximum value of the cuff pressure pulse wave during the elapsed times of 25 to 45 seconds, in the expression (4) above, thereby calculating the respiration-induced blood pressure fluctuation as a pressure value.

Figure 6:
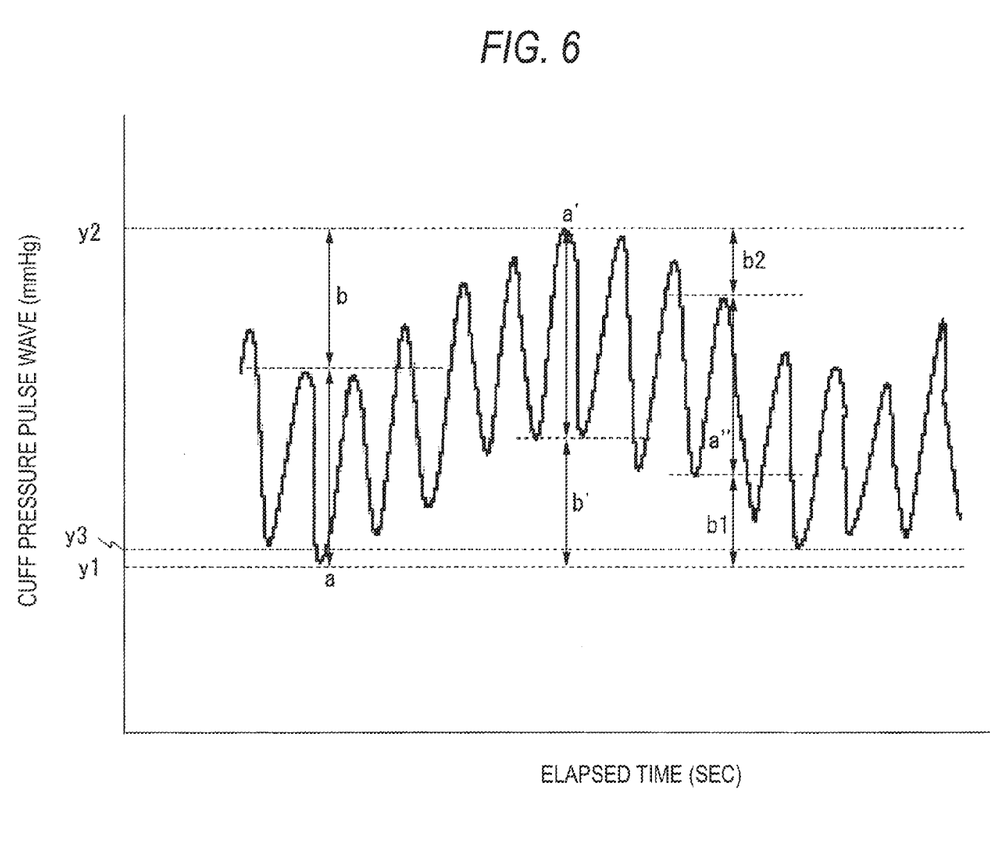
FIG. 6 is a diagram illustrating the cuff pressure pulse wave in one respiratory cycle in an enlarged manner.

The method of calculating the ratio is not limited to the calculation of the ratio X in which the amplitudes a and b shown in FIG. 5 are used. Other examples of the method of calculating the ratio X in the expression (4) above will be described with reference to FIG. 6. FIG. 6 is a diagram illustrating the cuff pressure pulse wave in one respiratory cycle in an enlarged manner.

As described above, the respiration-induced fluctuation calculating section 14 calculates the ratio X=(b/a) based on the amplitude a related to the minimum value (y1) of the cuff pressure pulse wave, and the amplitude b which is calculated by subtracting the upper limit value of the amplitude a from the maximum value (y2) of the cuff pressure pulse wave. Then, the respiration-induced fluctuation calculating section 14 multiplies the ratio X=(b/a) with the pulse pressure to calculate the respiration-induced blood pressure fluctuation as a pressure value.

Alternatively, the respiration-induced fluctuation calculating section 14 may calculate the ratio X=(b'/a') based on the amplitude a' related to the maximum value (y2) of the cuff pressure pulse wave, and the amplitude b' which is calculated by subtracting the minimum value (y1) of the cuff pressure pulse wave from the lower limit value of the amplitude a'. Then, the respiration-induced fluctuation calculating section 14 may multiply the ratio X=(b'/a') with the pulse pressure to calculate the respiration-induced blood pressure fluctuation as a pressure value.

The respiration-induced fluctuation calculating section 14 may calculate the ratio X which is to be multiplied with the pulse pressure, by using the maximum value (y2) of the cuff pressure pulse wave, the minimum value (y1) of the cuff pressure pulse wave, and an amplitude a", in terms of pressure value, of an optional pulse. That is, the respiration-induced fluctuation calculating section 14 may calculate the ratio X=((b1+b2)/a"), and multiply the ratio with the pulse pressure.

That is, the respiration-induced fluctuation calculating section 14 calculates the ratio X=(b/a) in the expression (4) by using the maximum value (first pressure value) and the minimum value (second pressure value) of the amplitude of the cuff pressure pulse wave in a given time period (preferably, one respiratory cycle), and an amplitude of a pulse in terms of pressure value (third pressure value). Here, the amplitude b, the numerator, is expressed by the following expression (5).

$$b = (\text{first pressure value} - \text{second pressure value}) - \text{third pressure value} \qquad (5).$$

In order to eliminate influence of outliers, for example, the second pressure value may be the lower limit value (e.g., y3 in FIG. 6) of the amplitude in which the peak has the second smallest value in amplitudes of the cuff pressure pulse wave in the given time period. This is applicable also to the first pressure value. That is, the respiration-induced fluctuation calculating section 14 is calculates a relationship (in the above-described example, the ratio) between the magnitude of the amplitude corresponding to the pulse pressure and the fluctuation width corresponding to the respiration-induced blood pressure fluctuation, and further calculate the respiration-induced blood pressure fluctuation as a pressure value by using this relationship.

The respiration-induced fluctuation calculating section 14 may statistically calculate the pulse amplitude a, the denominator in the expression (4). For example, the respiration-induced fluctuation calculating section 14 may calculate an average or a median amplitude of pulses in one respiratory cycle, as the pulse amplitude a used in the expression (4). This can eliminate influence of outliers, so that the respiration-induced fluctuation calculating section 14 can calculate the respiration-induced blood pressure fluctuation as a pressure value more accurately.

The expression (4) is merely an example, and the respiration-induced fluctuation calculating section 14 may calculate the respiration-induced blood pressure fluctuation of the subject as a pressure value in a different manner using the pulse pressure and the amplitude of the cuff pressure pulse wave. For example, the respiration-induced fluctuation calculating section 14 may adjust the value calculated by the expression (4) by multiplication or addition of a correction value to calculate the respiration-induced blood pressure fluctuation as a pressure value.

Figure 7A:
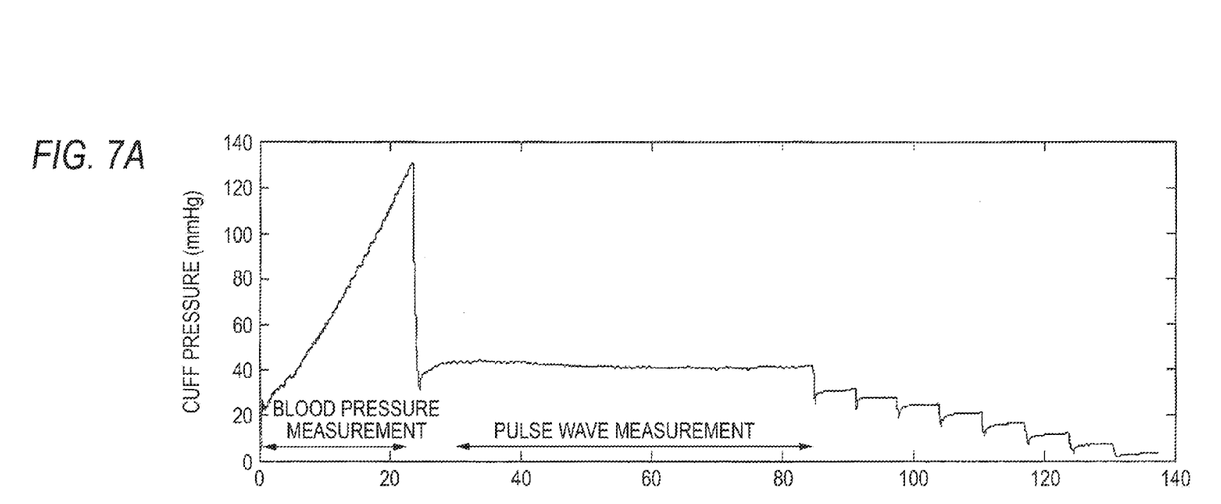
FIGS. 7A and 7B are diagrams illustrating changes in a cuff pressure in a series of processings in the measuring apparatus of FIG. 1.
Figure 7B:
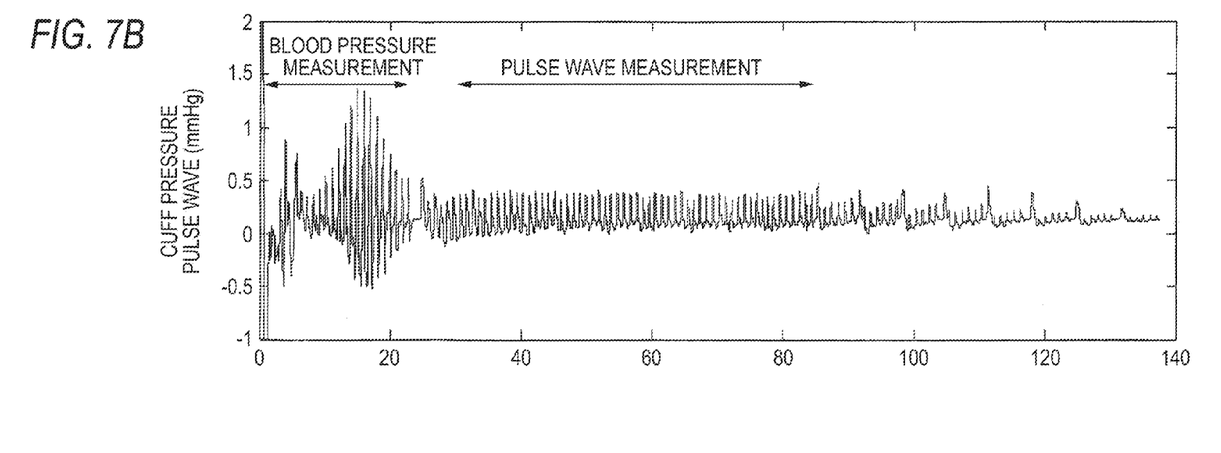

The flow of the calculation of the pulse pressure, the cuff pressure pulse wave, and the respiration-induced blood pressure fluctuation will be described with reference to FIGS. 7A and 7B. FIG. 7A is a diagram illustrating a transition of the cuff pressure in a series of processings, and FIG. 7B is a diagram illustrating a transition of the cuff pressure pulse wave. Firstly, the blood pressure calculating section 11 causes the pressure applied to a portion (e.g., the upper arm) of the subject to be raised by inflating the cuff 21 through the pressure controlling section 12. The blood pressure calculating section 11 detects oscillations which occur during the pressure rise of the cuff 21, thereby detecting the systolic blood pressure and the diastolic blood pressure. Namely, the blood pressure calculating section 11 calculates the pulse pressure before the measurement of the pulse wave. In FIGS. 7A and 7B, the blood pressure calculating section 11 calculates the systolic blood pressure and the diastolic blood pressure in a linear inflation mode (see, e.g., JP2012-40088A). The blood pressure calculating section 11 may calculate the systolic blood pressure and the diastolic blood pressure in a deflation mode (see, e.g., Bedside Monitor BSM-1700 series Life Scope PT, <www.nihonkohden.co.jp/iryo/products/monitor/01_beside/bsm1700.html> accessible as of Jan. 13, 2015). The blood pressure calculating section 11 calculates the pulse pressure based on the calculated systolic and diastolic blood pressures.

After the pulse pressure is calculated by the blood pressure calculating section 11, the pressure controlling section 12 lowers the cuff pressure. Here, the pressure controlling section 12 sets the cuff pressure to a predetermined value which is equal to or lower than the diastolic blood pressure calculated by the blood pressure calculating section 11, and which is supposed to be higher than the venous pressure. A pressure which is supposed to be higher than the venous pressure is 10 mmHg or higher. When the cuff pressure is set to be higher than the venous pressure, influence of the venous pressure can be canceled from the cuff pressure pulse wave. Since influence of the venous pressure is canceled, the measuring apparatus 1 can calculate an accurate respiration-induced blood pressure fluctuation as a pressure value without being affected by the venous pressure. In FIG. 7A, the pressure controlling section 12 sets the cuff pressure to about 40 mmHg, and then performs pressurization. After the setting of the cuff pressure, the pulse wave measuring section 13 measures the cuff pressure pulse wave. The respiration-induced fluctuation calculating section 14 calculates the respiration-induced blood pressure fluctuation as a pressure value by the method described above using the cuff pressure pulse wave and the pulse pressure.

As shown in FIGS. 7A and 7B, the measuring apparatus 1 consecutively executes the measurement of blood pressure (the systolic blood pressure, the diastolic blood pressure, and the pulse pressure) and the measurement of respiration-induced blood pressure fluctuation. By the consecutive measurements, the two kinds of measurements can be performed in a short time period. As shown in FIGS. 7A and 7B, the measuring apparatus 1 measures the pulse pressure after the blood pressure measurement. As indicated in Characteristic 1 above, a change of the arterial vascular volume and that of the blood pressure are linear in the range where the cuff pressure is equal to or lower than the diastolic blood pressure. In the case where the pulse wave is measured after the blood pressure is measured, the pressure controlling section 12 can accurately set the cuff pressure to be within the range not higher than the diastolic blood pressure. Therefore, the respiration-induced fluctuation calculating section 14 can calculate a respiration-induced blood pressure fluctuation as a pressure value more accurately.

Referring again to FIG. 1, the display section 15 displays the respiration-induced blood pressure fluctuation calculated as the pressure value by the respiration-induced fluctuation calculating section 14. For example, the display section 15 may be a liquid crystal display or the like provided on the housing of the measuring apparatus 1. In the case where the respiration-induced blood pressure fluctuation has an abnormal pressure value (or a value close to an abnormal value), for example, the display section 15 changes the display color to notify a doctor or the like of the abnormal state.

In the case where the measurement value of each parameter has an abnormal value (or a value near an abnormal value), the notifying section 16 outputs an alarm sound. In the case where the respiration-induced blood pressure fluctuation calculated by the respiration-induced fluctuation calculating section 14 is 12 mmHg or higher, for example, the notifying section 16 outputs an alarm sound.

Advantages of the measuring apparatus 1 according to the above exemplary embodiment will be described. As described above, there is a correlation between the amplitude of the cuff pressure and a change in the blood pressure. Based on this, the measuring apparatus 1 calculates the respiration-induced blood pressure fluctuation as a pressure value from the pulse pressure and the pulse wave (in the exemplary embodiment, the cuff pressure pulse wave). The pulse pressure is defined as the difference between the systolic and diastolic blood pressures that are calculated by the general oscillometric method or the like. The pulse wave can be easily acquired by, for example, a general blood pressure monitor using a cuff. The measuring apparatus can calculate the respiration-induced blood pressure fluctuation as a pressure value using only such general configurations for measuring the pulse pressure and the pulse wave. In other words, the measuring apparatus calculates the respiration-induced blood pressure fluctuation as a pressure value without a prior calibration or complicated process, and therefore, can perform a more practical measurement.

Next, a measuring apparatus according to another exemplary embodiment of the present invention will be described. The measuring apparatus 1 according to this exemplary embodiment acquires the pulse wave i using the principle of a pulse oximeter. Hereinafter, features that are different from the previously described exemplary embodiment will be described. In the following description, the processing sections designated by the same reference numerals as those of the previously described exemplary embodiment perform the same processings as those of the previously described exemplary embodiment, unless described otherwise herein.

The measuring apparatus 1 is configured such that the respiration-induced blood pressure fluctuation is calculated as a pressure value by using peripheral photoplethysmogram acquired based on the principle of a pulse oximeter. Peripheral photoplethysmogram is a volume pulse wave. It is known that peripheral photoplethysmogram has a similarity relationship to the blood pressure (see, e.g., Kirk H. Shelley, "Photoplethysmography: Beyond the Calculation of Arterial Oxygen Saturation and Heart Rate," International Anesthesia. Research Society, Vol. 105, No. 6, December 2007, S31-S36). Therefore, to calculate the respiration-induced blood pressure fluctuation as a pressure value, the measuring apparatus 1 treats the peripheral photoplethysmogram acquired based on the principle of a pulse oximeter equivalently to the cuff pressure pulse wave in the previously described exemplary embodiment.

Figure 8:
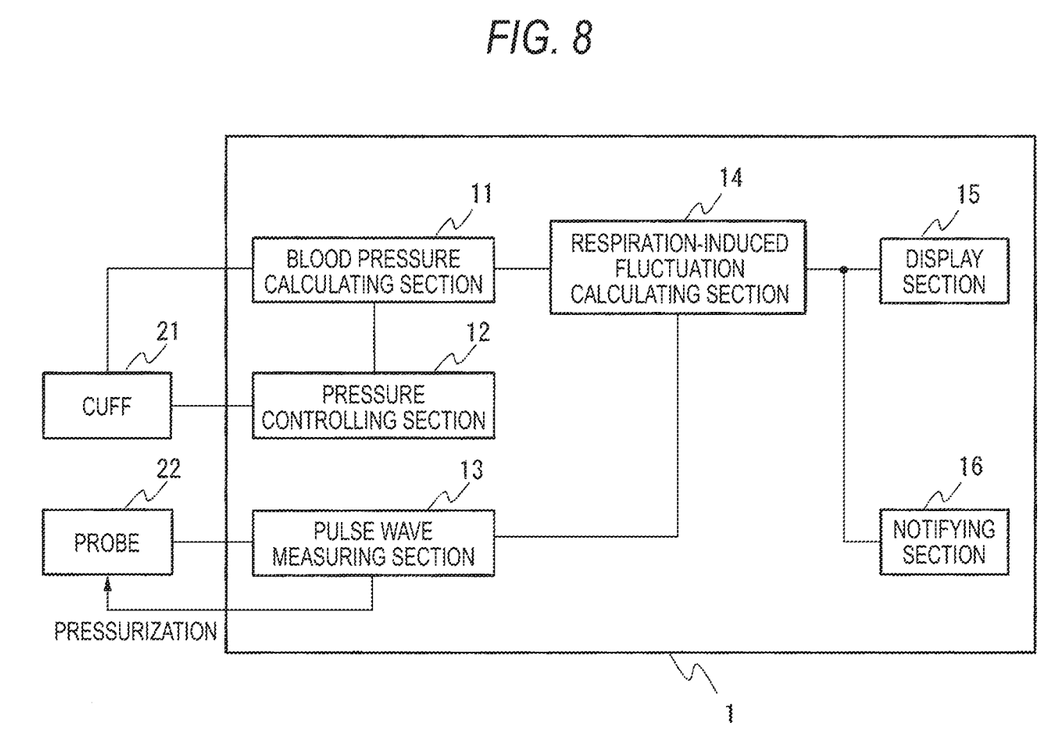
FIG. 8 is a block diagram of a configuration of a measuring apparatus according to another exemplary embodiment of the present invention.

FIG. 8 is a block diagram showing the configuration of the measuring apparatus 1. The measuring apparatus 1 is adapted to be connected with a probe 22 of the arterial oxygen saturation (SpO2) for measuring the pulse wave.

The probe 22 (pulse oximeter probe) is attached to the finger tip or ear lobe of the subject. The probe 22 has a light emitter and a light receiver. The probe 22 measures the arterial oxygen saturation (SpO2) by the principle of a general pulse oximeter. In general measurement of the arterial oxygen saturation (SpO2), application of a strong attachment pressure to a measurement portion should be avoided. This is because, in combination with slight heat generation due to light emission, the pressure application may possibly increase the physical burden on the subject.

Therefore, the pulse wave measuring section 13 controls the probe 22 so as to pressurize the attachment position of the subject only during measurement of the pulse wave. The probe 22 has an air bag or the line in, for example, the contact surface with the subject. The pulse wave measuring section 13 may perform pressurization by causing the air to flow into the air bag. Here, the pulse wave measuring section 13 controls the pressurizing force so as to be equal to or lower than the diastolic blood pressure, and equal to or higher than the venous pressure. Therefore, the pulse wave measuring section 13 can acquire the pulse wave from which influence of the venous pressure is canceled.

The processings performed by the respiration-induced fluctuation calculating section 14 is similar to those in the previously described exemplary embodiment, and therefore, a detailed description thereof will be omitted.

Advantages of the measuring apparatus 1 of this exemplary embodiment will be described. As described above, peripheral photoplethysmogram is a kind of volume pulse wave. Therefore, the measuring apparatus 1 calculates the respiration-induced blood pressure fluctuation as a pressure value by using peripheral photoplethysmogram. Peripheral photoplethysmogram can be non-invasively measured in a short time period by the principle of a general pulse oximeter. Therefore, the measuring apparatus 1 of this exemplary embodiment can also calculate the respiration-induced blood pressure fluctuation as a pressure value using only a general configuration for measuring the pulse pressure and the pulse wave.

Moreover, the pulse wave measuring section 13 controls the probe 22 so as to pressurize the predetermined position of the subject only during measurement of the pulse wave. Therefore, the burden on the predetermined position (mainly the finger tip) of the subject can be minimized.

While the present invention has been described with reference to certain exemplary embodiments thereof, the scope of the present invention is not limited to the exemplary embodiments described above, and it will be understood by those skilled in the art that various changes and modifications may be made therein without departing from the scope of the present invention as defined by the appended claims.

Although, in the above, the examples in which a cuff or an SpO2 probe is used in measurement of the pulse wave have been described, another technique may be used as far as it can measure the pulse wave of the subject. It has been described that the blood pressure calculating section 11 calculates the pulse pressure from the systolic blood pressure and the diastolic blood pressure. However, the blood pressure calculating section 11 may estimate the pulse pressure from one of the systolic blood pressure and the diastolic blood pressure.

The above-described processes of the blood pressure calculating section 11, the pulse wave measuring section 13, and the respiration-induced fluctuation calculating section 14 may be realized as computer programs which operate in the measuring apparatus 1. The programs may be stored in a non-transitory computer readable medium of any one of various types, and then supplied to the computer. The non-transitory computer readable medium includes tangible storage media of various types. Examples of the non-transitory computer readable medium are a magnetic recording medium (e.g., a flexible disk, a magnetic tape, and a hard disk drive), a magneto-optical recording medium (e.g., a magneto-optical disk), a CD-read only memory (CD-ROM), a CD-R, a CD-R/W, a semiconductor memory (e.g., a mask ROM, a programmable ROM (PROM), an erasable PROM (EPROM), a flash ROM, and a random access memory (RAM)). Alternatively, the programs may be supplied to the computer by means of a transitory computer readable medium of any one of various types. Examples of the transitory computer readable medium are an electrical signal, an optical signal, and an electromagnetic wave. The transitory computer readable medium can supply the programs to the computer through a wired communication path such as a metal wire or an optical fiber, or a wireless communication path.

What is claimed is:

1. A measuring apparatus comprising:
a blood pressure calculating section configured to calculate a pulse pressure of a subject;
a pulse wave measuring section configured to measure a pulse wave of the subject;
a respiration-induced fluctuation calculating section configured to:
calculate a respiration-induced blood pressure fluctuation of the subject as a pressure value, based on the pulse pressure and a fluctuation and an amplitude of the pulse wave in a given time period,
calculate a ratio of the respiration-induced blood pressure fluctuation to the pulse pressure, based on a maximum value and a minimum value of the pulse wave in the given time period and the amplitude, in terms of pressure value, of a pulse in the pulse wave, and
calculate the respiration-induced blood pressure fluctuation by multiplying the pulse pressure by said ratio; and
a display configured to display the respiration-induced blood pressure fluctuation and change a display effect when the respiration-induced blood pressure fluctuation contains an abnormal value.

2. The measuring apparatus according to claim 1, wherein the amplitude is an average or a median amplitude of pulses in the pulse wave in the given time period.

3. The measuring apparatus according to claim 1, wherein the given time period is one respiratory cycle of the subject.

4. The measuring apparatus according to claim 1, wherein the pulse wave measuring section is configured to measure the pulse wave in a state in which a portion of the subject is pressurized at a pressure equal to or higher than a pressure that is assumed to be higher than a venous pressure.

5. The measuring apparatus according to claim 1, wherein the blood pressure calculating section is configured to calculate the pulse pressure based on a systolic blood pressure and a diastolic blood pressure as detected by and acquired from a blood pressure cuff.

6. The measuring apparatus according to claim 1,
wherein the blood pressure calculating section is configured to calculate the pulse pressure before the measurement of the pulse wave, and
wherein the pulse wave measuring section is configured to measure the pulse wave consecutively after the calculation of the pulse pressure.

7. The measuring apparatus according to claim 1, wherein the pulse wave measuring section is configured to measure the pulse wave in a state in which a portion of the subject is pressurized at a pressure equal to lower than a diastolic blood pressure of the subject.

8. The measuring apparatus according to claim 1, wherein the pulse wave measuring section is configured to acquire the pulse wave from a pulse oximeter probe.

9. The measuring apparatus according to claim 8, wherein the pulse wave measuring section is configured to control the pulse oximeter probe to pressurize a portion of the subject only during an acquisition of the pulse wave.

10. A measuring method comprising:
calculating a pulse pressure of a subject;
measuring a pulse wave of the subject;
calculating a respiration-induced blood pressure fluctuation of the subject as a pressure value, based on the pulse pressure and a fluctuation and an amplitude of the pulse wave in a given time period;
calculating a ratio of the respiration-induced blood pressure fluctuation to the pulse pressure, based on a maximum value and a minimum value of the pulse wave in the given time period and the amplitude, in terms of pressure value, of a pulse in the pulse wave;
calculating the respiration-induced blood pressure fluctuation by multiplying the pulse pressure by said ratio; and
displaying the respiration-induced blood pressure fluctuation, wherein an effect of the displayed respiration-induced blood pressure fluctuation is changed when the respiration-induced blood pressure fluctuation contains an abnormal value.

11. A non-transitory computer readable medium storing a program that, when executed by a computer, causes the computer to execute a method comprising:
calculating a pulse pressure of a subject;
measuring a pulse wave of the subject;
calculating a respiration-induced blood pressure fluctuation of the subject as a pressure value, based on the pulse pressure and a fluctuation and an amplitude of the pulse wave in a given time period;
calculating a ratio of the respiration-induced blood pressure fluctuation to the pulse pressure, based on a maximum value and a minimum value of the pulse wave in the given time period and the amplitude, in terms of pressure value, of a pulse in the pulse wave;
calculating the respiration-induced blood pressure fluctuation by multiplying the pulse pressure by said ratio; and
displaying the respiration-induced blood pressure fluctuation, wherein an effect of the displayed respiration-induced blood pressure fluctuation is changed when the respiration-induced blood pressure fluctuation contains an abnormal value.

* * * * *